United States Patent [19]
Hodgkinson et al.

[11] Patent Number: 6,030,927
[45] Date of Patent: Feb. 29, 2000

[54] POST-HARVEST TREATMENT OF CROPS

[75] Inventors: Mark Cameron Hodgkinson, Mansfield; Gregory Birse, Broadview; David Johnson, Yeronga; Peter D. Taverner, Glenelg, all of Australia

[73] Assignee: Caltex, Australia Petroleum, Pty, Ltd., Sydney, Australia

[21] Appl. No.: 09/104,092

[22] Filed: Jun. 24, 1998

[30] Foreign Application Priority Data

Jun. 24, 1997 [AU] Australia .................................. PO7505

[51] Int. Cl.$^7$ .............................. A01N 27/00; A23B 5/00
[52] U.S. Cl. ............................. 504/357; 426/302
[58] Field of Search ................................ 426/302; 47/58, 47/DIG. 10, DIG. 11; 504/357

[56] References Cited

U.S. PATENT DOCUMENTS

| | | | |
|---|---|---|---|
| 4,165,230 | 8/1979 | Gravrok et al. | 71/127 |
| 4,388,297 | 6/1983 | Naffziger | 424/78 |
| 4,454,113 | 6/1984 | Hemker | 424/63 |
| 4,562,279 | 12/1985 | Heiba | 560/12 |
| 5,656,177 | 8/1997 | Werres | 210/764 |

FOREIGN PATENT DOCUMENTS

| | | | |
|---|---|---|---|
| 0 272 374 | 6/1988 | European Pat. Off. | A01N 25/24 |
| 55-167204A | 12/1980 | Japan | A01N 43/04 |
| 2 119 652 | 11/1983 | United Kingdom | A01N 25/02 |
| WO 85/02976 | 7/1985 | WIPO | A01N 25/02 |

*Primary Examiner*—Jose' G. Dees
*Assistant Examiner*—Alton Pryor
*Attorney, Agent, or Firm*—Welsh & Katz, Ltd.

[57] ABSTRACT

A post-harvest treatment method for eradication of biological infestation in crops comprises the step of applying post-harvest to the crop a petroleum oil that has a density at 15° C. in the range of 0.75 to 0.83 g/ml.

14 Claims, No Drawings

POST-HARVEST TREATMENT OF CROPS

FIELD OF THE INVENTION

The present invention relates to the post-harvest treatment of crops. More particularly, the invention relates to the application of petroleum derived oils and emulsions with specified characteristics to crops such as fruit and vegetables for treating biological infestations including pests, parasites, funguses, moulds, etc. The invention will be primarily described with reference to its use on citrus fruit and stone fruit but it should be appreciated that the invention also has application with the treatment of infestation in other fruit, vegetables, ornamental plants and other crops.

BACKGROUND OF THE INVENTION

Crops such as citrus, peaches, bananas and mangoes often become biologically contaminated post-harvest. Contamination can be initiated pre-harvest (eg. by parasitic presence at the time of picking/harvesting), during harvesting (eg. where contaminants are introduced by mechanical harvesters or human intervention) and post-harvest (eg. where parasites and spore settle on post-harvested produce).

Regardless of the time of contamination, it is desirable to treat harvested fruit, vegetables and plants prior to transportation and storage to eradicate any such contamination. For example, international quarantine regulations and inspection require fruit to be free of live pests. To this extent, post-harvest broad spectrum pesticides are currently applied to post-harvest produce, but there are international concerns with the residues of such pesticides on the fruit and vegetables so treated, especially the effects of such residues on humans.

SUMMARY OF THE INVENTION

Surprisingly, it has now been found that light and very light petroleum oils with certain characteristics can eradicate biological infestation when applied post-harvest to produce.

Accordingly, the present invention provides a post-harvest treatment method for eradication of biological infestation in crops comprising the step of applying post-harvest to the crop a petroleum oil that has a density at 15° C. in the range of 0.75 to 0.83 g/ml (inclusive).

Petroleum oils with a density in this range are generally referred to as light petroleum oils. In accordance with the invention, such oils have been found to have a capacity to efficiently cover, spread and/or penetrate various crops (especially fruit) to which they are applied so as to penetrate and thus exterminate pests, parasites, funguses, mould, bacteria etc.

Typically, the oil is applied in the form of an oil in water formulation, most preferably as an emulsion. One particularly preferred application of the oil is the post-harvest treatment of fruit with a calyx (eg. citrus fruit). However, other "crops" to which the invention can be applied include peaches, apples, kiwi fruit, mangoes, table grapes, ornamental plants including roses, berry fruit, lychees, avocadoes, star fruit, bananas etc; and vegetables including capsicum, tomatoes, pumpkin etc.

It is to be noted that various insects and larvae are small enough to conceal themselves under the calyx of citrus fruit, especially in oranges. Such pests can include light brown apple moth and mealy bug. The calyx has previously provided protection for the pests from contact pesticides applied pre-harvest. It is desirable that citrus be totally free of such pests, especially during transportation and storage (and especially for international fruit export), otherwise costly and potentially noxious fumigation procedures can become necessary. Light oils with the density range according to the invention have surprisingly been observed to have the capacity to spread and penetrate under the calyx to eradicate pests concealed thereunder.

Furthermore, with certain fruits, in particular citrus fruits, green mould (*penicillium digitatum*) can form on the fruit post-harvest. This is particularly so in the case of oranges. It has also been surprisingly discovered that the treatment of fruit with light petroleum oils having such density characteristics can eliminate or ameliorate the germination of penicillium spores.

The formulations can also be used to treat pathogens such as brown rot on peaches and anthracnose on mangoes and bananas, and also fungal bloom on grapes.

It has also been discovered that the stability of petroleum oil in water formulations, when held within certain ranges, can have efficacious application characteristics against pests, funguses, moulds, etc in crops which can then be efficiently treated post-harvest.

The present invention may also provide a post-harvest treatment method for eradication of biological infestation in crops comprising the step of applying post-harvest to the crop a petroleum oil in water formulation that has a cream/oil separation, as defined below, in the range of 0.25 ml to 3.0 ml inclusive. When the term "cream/oil separation" is used in the present specification, it is with reference to a 2%, 100 ml petroleum oil in a standard hard water emulsion in accordance with ASTM E1116. In accordance with this test procedure, after 20 minutes, it has been discovered that efficacious formulation characteristics are found in the range 0.25 ml to 3.0 ml of cream separation.

Typically, the oil is emulsified in the water to be present in a range of 1–6%, more typically at about 3% by total volume, but in other applications (eg. for crops with blooms, such as mangoes and grapes) can range down to as low as 100–1000 μl/L.

When dipping is used as the application technique, typically a lower treat rate in the formulation provides effective oil coverage of the crop so dipped. When the application technique employed is spraying, typically a formulation is required that is more concentrated than that used for dipping, so that satisfactory efficacy is maintained, and yet in-line processing equipment contamination with the oil is minimised.

Typically when the formulation is an emulsion it can include a humectant and an emulsifier. The use of a humectant reduces water loss from treated fruit and vegetables; (ie. the water loss may sometimes be induced by certain petroleum derived oils). A typical humectant employed is glycerol mono-oleate.

The emulsifier is selected to give desirable emulsifying characteristics to petroleum oil in water formulations. For example, emulsifiers such as polyoxyethylene sorbitan trioleate, sorbitan mono-oleate, cetyl-oleyl alcohol and mono-oleate polyoxyethylene sorbitan impart desirable emulsifying characteristics. Emulsifiers such as polyoxyethylene sorbitan trioleate or sorbitan mono-oleate are physically and chemically compatible with the paraffinic base oil, being stable in the oil and imparting emulsibility to the oil.

Emulsifier treat rate (content) in the formulation is also varied dependent on the application (crop or application method) to optimise breaking characteristics so that desired oil coverage is achieved. The emulsifier is preferably of food grade standard when used with crops for human consumption.

Preferably the oil employed is a food grade aliphatic hydrocarbon, and is typically a light paraffinic oil that ranges in carbon chain length from C12 up to C22 (although chain length is not ultimately in itself a characterising feature). In the case of fruit treatment, aliphatic hydrocarbons of chain length around C14–C18 are preferred, and hydro-carbons of C15 chain length are particularly preferred. Oils such as Citrole (C19) can also be employed.

Light paraffinic oils have the advantage of low viscosity which can aid in penetrating difficult to access regions on crop surfaces (eg. under the calyx of citrus fruit).

MODES FOR CARRYING OUT THE INVENTION

Notwithstanding any other forms which may fall within the scope of the present invention, various preferred forms of the invention will now be described with reference to the following non-limiting examples.

Post-Harvest Treatment of Citrus Fruit for the Elimination of Mealybug and Light Brown Apple Moth The need for the elimination of these pathogens arose because the use of post-harvest broad spectrum pesticides (other than fungicide and wax baths) was (and is currently) not allowed with export fruit (eg to the USA) due to concerns over residues. Many growers were moving back to liberal applications of broad spectrum pesticides in the field (ie. pre-harvest) in the hope of delivering pest free fruit to processors.

In accordance with the present invention, various formulations were applied post-harvest to citrus fruit to test the efficacy against insect pests infecting the same. These formulations are tabulated in the Examples below.

The calyx of citrus fruit was observed to provide a protective shelter for a range of small arthropods, including light brown apple moth (LBAM) (*epiphyas postvittana*). LBAM spins a silken domicile that is hydrophobic and thus many LBAM larvae survive prior art washing processes prior to packing so that the larvae develop in storage.

Experiments were conducted to identify a treatment which ensured 100% eradication of mealybug and light brown apple moth from citrus fruit in post-harvest processing facilities.

Treatments were applied using a dipping bath (mean volume=2,500 L) at a rate of 5% (ie. 250 L) where the bath was renewed after treatment of 80 tonne of citrus. The expected citrus mass to be treated each growing season was assumed to be 10,000 tonne (which thus equated to an estimated 15,000 L of product).

EXAMPLE 1

| Component | PCM No. | CAS No. | Volume % |
| --- | --- | --- | --- |
| Light solvent extracted, dewaxed and hydrotreated paraffinic oil | 1022 | 74742-56-9 | 92.3 |
| Polyethylene glycol dioleate | 2564 | 9005-07-6 | 5.56 |
| Sorbitan mono-oleate | 2023 | 1338-43-8 | 1.28 |
| Water | | | low |

EXAMPLE 2
Food Grade Oil Plus Surfactants Graded for Incidental Contact with Food

| Component | CAS No. | Volume % |
| --- | --- | --- |
| White mineral oil (Medicinal Paraffin) | 8042-47-5 | 94 |
| Cetyl-oleyl alcohol condensed with 3 moles of ethylene oxide | 68439-49-6 | 4.8 |
| Polyethylene (20) sorbitan trioleate | 9005-70-3 | 1.2 |

EXAMPLE 3
Food Grade Oil Plus Food Grade Surfactants

| Component | CAS No. | Volume % |
| --- | --- | --- |
| White mineral oil (Medicinal Paraffin) | 8042-47-5 | 90 |
| Mono-oleate polyoxyethylene sorbitan | 9005-65-6 | 6.2 |
| Sorbitan mono-oleate | 1338-43-8 | 3.8 |

EXAMPLE 4
Food Grade solvent Plus Surfactants Graded for Incidental Contact with Food

| Component | CAS No. | Volume % |
| --- | --- | --- |
| Paraffinic (C15) solvent <0.03 wt % aromatics <5 ppm sulphur | 64771-72-8 | 80 |
| Cetyl-oleyl alcohol condensed with 3 moles of ethylene oxide | 68439-49-6 | 7.2 |
| Polyoxyethylene (20) sorbitan trioleate | 9005-70-3 | 4.8 |

EXAMPLE 5
Food Grade Solvent Plus Food Grade Surfactants

| Component | CAS No. | Volume % |
| --- | --- | --- |
| Paraffinic (C15) solvent <0.03 wt% aromatics <5 ppm sulphur | 64771-72-8 | 80 |
| Mono-oleate polyoxyethylene sorbitan | 90058-65-6 | 10.4 |
| Sorbitan mono-oleate | 1338-43-8 | 9.6 |

EXAMPLE 6

| Component | CAS No. | Vol % | Mass % |
| --- | --- | --- | --- |
| C15 aliphatic hydrocarbon/active constituent | 64771-72-8 | 87.12 | 85.2 |
| Food grade, paraffinic base oil/masking agent | NA | 9.16 | 10 |

-continued

| Component | CAS No. | Vol % | Mass % |
|---|---|---|---|
| glycerol mono-oleate/ humectant-water absorber | NA | 0.99 | 1.2 |
| Polyoxyethlene (20) sorbitan trioleate surfactant/ emulsifier | 9005-70-3 | 2.73 | 3.6 |

Bioassay work was undertaken to compare low toxicity insecticidal soap products (Natrasoap, Spray Tech Pty Ltd) against the above formulations (Examples 1 to 6). The formulations in the Examples were found to be far superior to existing soap products.

For Examples 1 to 3, initial mortality studies on exposed light brown apple moth were promising when the product was used at 5% in water (Table 1). However, latter work on insects hidden under the calyx of oranges identified that Examples 4, 5 and 6 were superior. This was attributed to the lower density of the base oil used in Examples 4 to 6 as opposed to the oil used in the first three formulations. Formulation 4 was appealing, being a very stable emulsion but was not very efficacious unless used at very high treat rates, Formulation 5 provided a very quick breaking emulsion which was surmised to have applications with other crops (ie. other than citrus dipping). Formulation 6 was the most suitable as a post-harvest spray and post-harvest dip for citrus fruit, and analysis confirmed that Formulation 6 had the best oil deposition behaviour (FIG. 1).

Acceptable oil-in-water volume % ranges in the formulations were found to be from about 1% to about 6%.

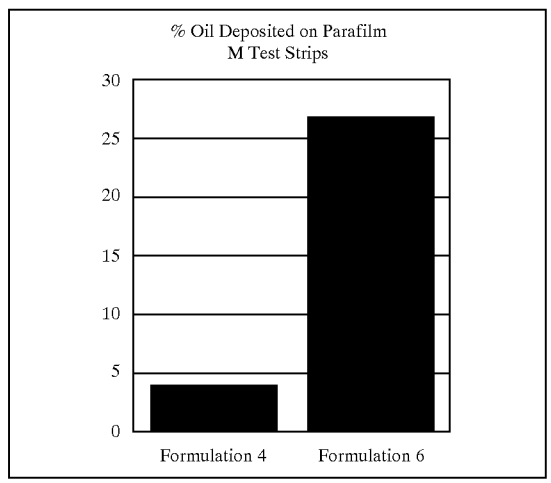

FIG. 1: % oil deposited on test strips.

Further, the following rates of mortality were observed for the various formulations.

TABLE 1

Mortality of exposed light brown apple moth (stage 3 larvae) (n = 10) when treated with formulations of the invention

| Example | Mortality @ 5% dose rate, 30 second dip. | Mortality @ 1% dose rate, 30 second dip |
|---|---|---|
| 1 | 100 | 25 |
| 2 | 100 | 35 |
| 3 | 100 | 57 |
| 4 | 100 | 100 |
| 5 | 100 | 100 |
| 6 | 100 | 100 |

Note: Mortality of untreated controls was 0%.

Field Trial

A confidential field trial of formulations 5 and 6 was carried out in a 1,000 L bath and each formulation was used to treat one crate of citrus fruit. The trials were successful in that 100% control of insect pests was obtained and no detrimental effect on fruit quality was perceived. Further, the fruit was let stand for 24 hours post dip and was then processed in the normal way. Oil dipped fruit gave a better appearance after waxing than did control fruit and initial long term storage tests indicated that treated oranges had a better "orange colour" than control fruit. This was surmised to be due to enhanced ethylene production in the treated fruit. Also, no adverse taste perception was noticed.

Details of Formulation Components

The preferred use of the formulations was in dipping baths with continual mixing. Thus, the emulsion characteristic of "good strike" was most important. An emulsion with good strike was one that displayed easy mixing and an even milky appearance. A desirable quality of the formulation when used for citrus treatment was its capacity for enhanced ingress under the fruit calyx. It was seen to be an advantage if the emulsion did not break between treatment of crates of citrus fruit.

The choice of surfactants was confined to those which were either food grade quality or graded safe for incidental contact with food. All formulations were observed to be stable with respect to phase separation at 0° C., 20° C. and 43° C.

Blending of Formulations 4, 5 and 6 required no special techniques and was simply a matter of adding the appropriate amount of surfactant to the C15 oil and mixing until a clear solution was obtained.

Comparative Example 1

The preferred Formulation 6 was then compared against a commercial C23 petroleum spray oil to test for efficacy against light brown apple moth. Five treatment rates were selected to give a range of mortalities, with the rate selected for both the C23 oil and the preferred formulation being 1, 2.5, 5, 10 and 25 ml/liter.

Groups of ten infested oranges were suspended in a 500 ml beaker of emulsion for 30 seconds, with the emulsion being well agitated prior to dipping. After treatment, infested fruit were placed on trays to drain for 5 minutes, and larva were then removed from under the calyx and placed into a plastic container for rearing. Any larva found dead immediately after treatment were counted and discarded.

FIG. 2 plots mortality against oil dip concentration and shows 1 plot of the preferred formulation (triangle point results) and a second plot of the C23 treatment rate (circular point plots) against a mortality scale figure.

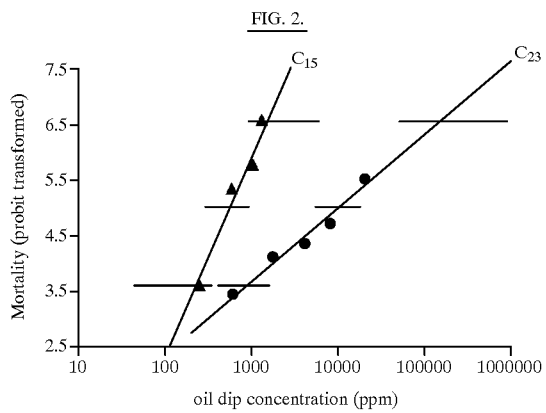

FIG. 2.

From FIG. 2, it can be seen that a very low concentration of the preferred formulation provided a high mortality, whereas considerably more concentrated (and therefore uneconomical) dose rates were required for the C23 oil.

Table 2 lists the percentage mortality for three developmental stages for light brown apple moth when dipped in a preferred formulation according to the present invention, at varying treatment rates.

TABLE 2

| Rate (ml liter$^{-1}$) | Egg age (days) | Total Eggs* | Eggs unhatched | % Mortality ± SEM |
|---|---|---|---|---|
| 0 | 2 | 253 | 34 | 13.4 ± 5.8 |
| | 7 | 299 | 27 | 9.0 ± 3.2 |
| | 10 | 248 | 29 | 11.7 ± 2.7 |
| 0.1 | 2 | 264 | 175 | 66.3 ± 2.7 |
| | 7 | 312 | 17 | 5.4 ± 2.2 |
| | 10 | 263 | 135 | 51.3 ± 19.4 |
| 1.0 | 2 | 265 | 265 | 100.0 ± 0.0 |
| | 7 | 301 | 73 | 24.3 ± 14.7 |
| | 10 | 274 | 253 | 92.3 ± 1.2 |
| 5.0 | 2 | 248 | 248 | 100.0 ± 0.0 |
| | 7 | 306 | 306 | 100.0 ± 0.0 |
| | 10 | 316 | 316 | 100.0 ± 0.0 |

*Values are the sum of 6 eggmasses.

Treatment of Green Mould on Citrus Fruit

The biocontrol properties of various emulsions (primary formulations 4, 5 and 6) were tested against green mould (*Penicillium digitatum*) in oranges. Two experiments were conducted to test these properties. Experiment No. 1 tested for localised biocontrol where the suspensions were directly pipetted into wounds. In experiment No. 2, fruit were dipped into the proposed biocontrol solution.

EXAMPLE 7—Experiment No. 1

Localised Biocontrol

Aim: Assessing biocontrol activity of the oil by directly pipetting oil and spores into wounds.

Treatments:

1. unwounded control
2. wounded only control
3. wounded, oil emulsion, spore suspension
4. wounded, spore suspension, oil emulsion
5. wounded, oil emulsion, wait 2 hrs, spore suspension
6. wounded, spore suspension, wait 2 hrs, oil emulsion
7. wounded, oil emulsion, wait 24 hrs, spore suspension
8. wounded, spore suspension, wait 24 hrs, oil emulsion
9. wounded, spore suspension
10. wounded, wait 2 hrs, spore suspension
11. wounded, wait 24 hrs, spore suspension Method: 110 (10 reps of 1 fruit/treatment; 2 wounds/fruit) Valencia oranges with normal post-harvest treatments were surface sterilised with 70% ethanol, allowed to dry, wounded with a sterile nail to make a wound size of 3mm wide×5 mm deep, and inoculated with the oil and Penicillium spores. The oil treatment was 3% in water to make an emulsion, which was stirred constantly. 5 $\mu$l of this was pipetted/wound. The spore inoculum was washed spores of *Penicillium digitatum* at a concentration of $1\times10^6$ spores/ml. 5 $\mu$l of this suspension was pipetted into each wound.

Fruit were assessed every day for incidence and severity of disease. (Severity being defined as the average diameter of the lesion in mm).

TABLE 3

Results: Incidence = % of wounds with disease.

| Treatment | 4 days % | 5 days & | 6 days % | 7 days % |
|---|---|---|---|---|
| 1. unwounded | 0 | 0 | 0 | 0 |
| 2. wounded only | 0 | 0 | 0 | 0 |
| 3. wound, oil, spores | 0 | 0 | 0 | 0 |
| 4. wound, spores, oil | 0 | 0 | 0 | 0 |
| 5. wound, oil, 2 hrs, spores | 0 | 0 | 0 | 0 |
| 6. wound, spores, 2 hrs, oil | 0 | 0 | 0 | 0 |
| 7. wound, oil, 24 hrs, spores | 0 | 0 | 0 | 0 |
| 8. wound, spores, 24 hrs, oil | 25 | 50 | 50 | 55 |
| 9. wound, spores | 15 | 40 | 50 | 50 |
| 10. wound, 2 hrs, spores | 20 | 40 | 50 | 50 |
| 11. wound, 24 hrs, spores | 15 | 45 | 50 | 50 |

TABLE 4

Severity - average diameter of lesions in mm.

| Treatment | 4 days mm | 5 days mm | 6 days mm | 7 days mm |
|---|---|---|---|---|
| 1. unwounded | 0 | 0 | 0 | 0 |
| 2. wounded only | 0 | 0 | 0 | 0 |
| 3. wound, oil, spores | 0 | 0 | 0 | 0 |
| 4. wound, spores, oil | 0 | 0 | 0 | 0 |
| 5. wound, oil, 2 hrs, spores | 0 | 0 | 0 | 0 |
| 6. wound, spores, 2 hrs, oil | 0 | 0 | 0 | 0 |
| 7. wound, oil, 24 hrs, spores | 0 | 0 | 0 | 0 |
| 8. wound, spores, 24 hrs, oil | 2.650 ± 1.440 | 10.200 ± 3.89 | 23.40 ± 8.04 | 33.00 ± 10.7 |

TABLE 4-continued

Severity - average diameter of lesions in mm.

| Treatment | 4 days mm | 5 days mm | 6 days mm | 7 days mm |
|---|---|---|---|---|
| 9. wound, spores | 1.500 ± 0.764 | 7.050 ± 3.04 | 19.90 ± 7.66 | 30.25 ± 10.2 |
| 10. wound, 2 hrs, spores | 2.000 ± 1.110 | 8.450 ± 3.77 | 20.80 ± 8.04 | 30.00 ± 10.3 |
| 11. wound, 24 hrs, spores | 1.500 ± 1.070 | 8.100 ± 3.67 | 19.15 ± 7.21 | 30.25 ± 10.2 |

TABLE 5

Summary results - severity.

| Treatment | 4 days mm | 5 days mm | 6 days mm | 7 days mm |
|---|---|---|---|---|
| 1. oil | 0.442 ± 0.263 | 1.700 ± 0.794 | 3.90 ± 1.71 | 5.50 ± 2.34 |
| 2. no oil | 1.667 ± 0.554 | 7.867 ± 1.960 | 19.95 ± 4.26 | 30.17 ± 5.71 |

From table 3, it can be seen that no disease was recorded for the control treatments (unwounded and wounded only); for wounded+oil+spores; for wounded+spores+oil; for wounded+oil+wait 2 hrs then spores; for wounded+spores+wait 2 hrs then oil and for wounded+oil+wait 24 hrs then spores. The treatments where disease did occur were in wounded+spores+wait 24 hrs then oil; wounded+spores; wounded+wait 2 hrs then spores and in wounded+wait 24 hrs then spores. From table 3, the percentage incidence did not vary significantly for the treatments where *Penicillium digitatum* produced green mould in the oranges.

Table 4 shows the severity, giving the average diameter of the lesion recorded for each treatment. The average diameter of the lesions did not vary significantly between those treatments where disease occurred.

Table 5 is a summary of results, combining all the treatments which were treated with the oil emulsion and combining all treatments which did not have the oil. After 7 days, the average lesion diameter for fruit not treated with the oil emulsion was 30.17±5.71 mm. The average diameter of the lesions for fruit that were treated with the oil was 5.50±2.34 mm. This result of 5.50±2.34 mm was due solely to the treatment of wound+spores+wait 24 hrs then oil.

Conclusion

From these results, the various oil emulsions were shown to have biocontrol properties against green mould of orange when pipetting the oil emulsion and spore suspension directly into the wounds. The only treatment where the oil did not control the disease was for treatment 8–wound+spores+wait 24 hrs then oil. This was because the disease already had a hold on the fruit during the 24 hrs before the oil was applied.

EXAMPLE 8—Experiment No. 2
Biocontrol by Dipping Fruit in the Oil Emulsion
Aim: Assessing biocontrol activity of various formulations by dipping.
Treatments:
1. wounded only
2. wounded, oil dip
3. wounded, spore suspension
4. wounded, oil dip, spore suspension
5. oil dip, wounded
6. oil dip, wounded, spore suspension
7. wounded, spore suspension, oil dip Method: 112 (8 reps of 2 fruit/treatment; 2 wounds/fruit) Valencia oranges with no post-harvest treatment were surface sterilised with 70% ethanol and allowed to dry. Dipping was done for 30 seconds in a shallow bucket on a magnetic stirrer; 2 fruit were dipped at one time. Dipped fruit were then left to dry. Wounding was done with a sterile nail to make a wound size of 3 mm wide×5 mm deep. The spore inoculum was washed spores of *Penicillium digitatum* at a concentration of $3 \times 10^5$ spores/ml. 5 µL of this suspension was pipetted into each wound.

Fruit were assessed every second day for incidence and severity of disease. Severity being the average diameter of the lesion in mm.

TABLE 6

Incidence - % of wounds with disease.

| Treatment | 3 days % | 5 days % | 7 days % |
|---|---|---|---|
| 1. wounded only | 0 | 0 | 0 |
| 2. wound, oil dip | 0 | 0 | 0 |
| 3. wound, spores | 100.0 | 100 | 100 |
| 4. wound, oil dip, spores | 53.0 | 100 | 100 |
| 5. oil dip, wound | 0 | 0 | 0 |
| 6. oil dip, wound, spores | 84.0 | 100 | 100 |
| 7. wound, spores, oil dip | 62.5 | 100 | 100 |

TABLE 7

Severity - diameter of lesions in mm.

| Treatment | 3 days mm | 5 days mm | 7 days mm |
|---|---|---|---|
| 1. wounded only | 0 | 0 | 0 |
| 2. wound, oil dip | 0 | 0 | 0 |
| 3. wound, spores | 11.09 ± 0.65 | 28.69 ± 1.42 | 44.87 ± 1.79 |
| 4. wound, oil dip, spores | 3.81 ± 1.09 | 23.62 ± 0.61 | 39.19 ± 1.31 |
| 5. oil dip, wound | 0 | 0 | 0 |
| 6. oil dip, wound, spores | 7.25 ± 0.81 | 26.12 ± 1.85 | 40.62 ± 0.90 |
| 7. wound, spores, oil dip | 4.84 ± 0.86 | 23.37 ± 1.37 | 38.47 ± 1.75 |

From table 6, it can be seen that no disease was recorded for the control treatments (wounded only; wound+oil dip and oil dip+wound). For the wound+spores treatment, all wounds had disease (100%) at just 3 days after inoculating. For 3 treatments with the oil (wound+oil dip+spores; oil dip+wound+spores and wound+spores+oil dip) and after 3 days the incidence was 53, 84 and 62.5% respectively. All treatments causing disease with the oil dipping and spores had significantly less disease than the wound+spores treatment.

Table 7 verifies the results already discussed giving the average diameter of the lesions. At 7 days the fruit with the treatment wounded+spores gave the highest average diameter of lesions of 44.87±1.79 mm.

Conclusion

From these results, it was concluded that the preferred oil emulsions did have biocontrol properties against green mould of orange when the oranges were dipped into the oil emulsion. The treatments with oil dipping and spores slowed down the disease by up to 2 days, compared with the spores alone.

Comparison of Experiments

In experiment 1, (pipetting directly into wounds), reached up to 55%, whereas in experiment 2, (fruit dipped in oil emulsion), the incidence reached up to 100% 3 days after inoculating. This difference was surmised to be due to a difference in quality of the fruit and the fruit from experiment 2 had no post-harvest treatments of fungicides etc, thus making it more susceptible to disease.

Greater control by the oil was obtained in experiment 1 compared with experiment 2. In experiment 1, the oil emulsion and spores were directly pipetted into a small wound 3 mm wide×5 mm deep. In experiment 2, the fruit were only dipped in the oil emulsion. In experiment 1, the oil was in closer proximity to spores and possibly caused a barrier in the wound to not allow the spores to infect the fruit. This may account for the greater control recorded for experiment 1.

General Conclusion on Treatment of Green Mould

From the results of these two experiments, it can be seen that the preferred oil emulsions of the invention protected oranges against green mould caused by *Penicillium digitatum* when spores and oil were pipetted into wounds or when fruit was dipped into the oil emulsion.

Post-Harvest Treatment of Peaches, Mangoes and Bananas for the Elimination of Brown Rot and Anthracnose (respectively)

Peach Monilinia spp.(brown rot) was treated post harvest with preferred formulations according to the present invention (including in particular formulation 6). The treatment regime used involved inoculating fungal spores into wounds in the peaches and surface inoculating onto non-wounded peaches. The peaches were oil dipped either before or after inoculation. The preferred oil demonstrated excellent results for surface treatment although lesser results were demonstrated on the wounded treatments.

It was noted that wounding is a likely worse case scenario in practical commercial applications and that pathogen treatment for wounded peaches can be improved with further formulation optimisation. It was also noted that some surface spores were most likely simply washed off by the emulsion without any anti-fungal action needing to take place. Results of three typical treatments are provided below.

A similar methodology was used for the post-harvest treatment of mango and banana Colletotrichum gloeosporioides (anthracnose) and promising elimination of the pathogen by preferred formulations was observed. It was noted that further and better target treatment regimes can be developed (because the experimental work was conducted using one rate of infection, one oil concentration and one dipping time). These parameters were altered to ensure that preferred oils were used optimally in differing post harvest applications.

EXAMPLE 9

Materials and Methods

Clean, non-fungicide treated, Victorian Somerset peaches were surface sterilised with 70% ethanol and allowed to air dry. 15 fruit per treatment were inoculated on the surface (once for each fruit) with 25 liters of unwashed spore suspension of Monilinia fructicola at 5×106 spores/ml. The fruit was then allowed to air dry before being dipped, two at a time, in a constantly stirred 3% emulsion of the preferred oil for 30 seconds. Fresh oil emulsion was used for each treatment. After inoculation the fruit was incubated at 20° C. in cardboard trays. Each tray was placed in wet black plastic garbage bags for the first 48 hours to gain a higher humidity environment. The fruit was assessed for appearance of disease (ie. incidence) and lesion diameter was measured (mm).

Results

No disease was recorded for the uninoculated control treatments. Results are summarised in the following Tables 8 and 9.

TABLE 8

Incidence (%; n = 15) of brown rot on Somerset peaches.

| Treatment Number | Treatment Description | Day 2 | Day 4 | Day 6 | Day 9 |
|---|---|---|---|---|---|
| 1 | Uninoculated control | 0 | 0 | 0 | 0 |
| 2 | Surface inoculation, no oil treatment | 0 | 0 | 14 | 39 |
| 3 | Surface inoculation, dip in oil emulsion (30 sec) | 0 | 0 | 0 | 0 |

TABLE 9

Severity of brown rot (lesion diameter, mm; mean standard error; n = 15) on Somerset peaches.

| Treatment Number | Treatment Description | Day 2 | Day 4 | Day 6 | Day 9 |
|---|---|---|---|---|---|
| 1 | Uninoculated control | 0.0 | 0.0 | 0.0 | 0.0 |
| 2 | Surface inoculation, no oil treatment | 0.0 | 0.0 | 38 +/− 2.9 | 19.8 +/− 8.3 |
| 3 | Surface inoculation, dip in oil emulsion (30 sec) | 0.0 | 0.0 | 0.0 | 0.0 |

A similar experimental regime was adopted for mango and banana anthracnose post-harvest treatment, and a similar results profile was observed.

Treatment of Other Crops

Experiments were conducted using various petroleum derived oils of length C12 to C22 (eg. light paraffinic oils, light naphthenic, citroles etc) on various other fruits, vegetables and plants including apples, mangoes, grapes; ornamentals including roses; and capsicum, tomatoes and pumpkin. Where bloom quality (the frosty external appearance on the crop) was important in the crop (eg. with mangoes and table grapes), very low treatment rates (100–1000µl/L) were used in dips. Longer application times were then employed whilst still achieving excellent levels of eradication. Higher application rates and shorter dip times were observed to be suitable for most other applications.

To optimise the coverage from a low application rate, various surfactants (spreaders) and rates, different density oils and different emulsion break characteristics were investigated. In particular, surfactants that reduced surface tension of the oil on the surface of the crop (eg. fruit) were preferred.

Whilst the invention has been described with reference to a number of preferred embodiments, it should be appreciated that the invention can be embodied in many other forms.

We claim:

1. A post-harvest treatment method for eradication of biological infestation in harvested crops comprising applying to the harvested crop a petroleum oil that has a density at 15° C. in the range of 0.75 to 0.83 g/ml.

2. A method as claimed in claim 1 wherein the oil is applied as an oil in water formulation.

3. A method as claimed in claim 2 wherein the formulation is an emulsion used for the post-harvest treatment of fruit with a calyx and applied thereto by dipping or spraying the fruit with the emulsion.

4. A method as claimed in claim 3 wherein the oil is present in the water at about 3% by total volume.

5. A method as claimed in claim 2 wherein the crop comprises a bloom and the oil is present in the water in the range 100–1000 $\mu$l/L.

6. A method as claimed in claim 2 wherein the formulation further includes a humectant and an emulsifier.

7. A method as claimed in claim 6 wherein the humectant is glycerol mono-oleate.

8. A method as claimed in claim 6 wherein the emulsifier is polyoxyethylene sorbitan trioleate, sorbitan mono-oleate, cetyl-oleyl alcohol, or mono-oleate polyoxyethylene sorbitan.

9. The method as claimed in claim 1 wherein the petroleum oil is a food grade aliphatic hydrocarbon.

10. A post-harvest treatment method for eradication of biological infestation in a crop comprising applying petroleum oil that has a density at 15° C. in the range of 0.75 to 0.83 g/ml to the harvested fruit with a calyx, wherein the petroleum oil is applied as an oil in water emulsion formulation in which the oil is present in the water at about 3% by total volume, and the petroleum oil is applied by dipping or spraying the fruit with the emulsion.

11. A post-harvest treatment method for eradication of biological infestation in a harvested bloom comprising applying petroleum oil that has a density at 15° C. in the range of 0.75 to 0.83 g/ml to the harvested bloom, wherein the petroleum oil is applied as an oil in water formulation in which the oil is present in the water in the range 100–1000 $\mu$l/l.

12. A post-harvest treatment method for eradication of biological infestation in a crop comprising applying petroleum oil that has a density at 15° C. in the range of 0.75 to 0.83 g/ml to the havrvested crop, wherein the oil is applied as an oil in water formulation that further includes a humectant and an emulsifier.

13. The method according to claim 12 wherein the humectant is glycerol mono-oleate.

14. The method according to claim 12 wherein the emulsifier is polyoxyethylene sorbitan trioleate, sorbitan mono-oleate, cetyl-oleyl alcohol, or mono-oleate polyoxyethylene sorbitan.

* * * * *